(12) United States Patent
Higuchi et al.

(10) Patent No.: US 6,375,664 B1
(45) Date of Patent: Apr. 23, 2002

(54) MANDRIN OF MEDICAL ANESTHETIC NEEDLE AND METHOD OF MANUFACTURING SAME

(75) Inventors: Akio Higuchi; Hayato Hyugaji, both of Tokyo (JP)

(73) Assignee: Dr. Japan Co., Ltd., Tokyo (JP)

( * ) Notice: Subject to any disclaimer, the term of this patent is extended or adjusted under 35 U.S.C. 154(b) by 0 days.

(21) Appl. No.: 09/446,917
(22) PCT Filed: Jul. 28, 1997
(86) PCT No.: PCT/JP97/02595
§ 371 Date: Dec. 30, 1999
§ 102(e) Date: Dec. 30, 1999
(87) PCT Pub. No.: WO99/04843
PCT Pub. Date: Feb. 4, 1999

(51) Int. Cl.[7] ............................................. A61B 17/34
(52) U.S. Cl. ...................................... 606/185; 606/170
(58) Field of Search ................................ 606/184, 185, 606/170, 167, 180; 604/22

(56) References Cited

U.S. PATENT DOCUMENTS 5,766,200 A * 6/1998 Mazurek et al. ............ 606/170
6,120,519 A * 9/2000 Weber et al. ................ 606/170

FOREIGN PATENT DOCUMENTS

JP   A 59051862   3/1984
JP   A 05269205   10/1993

* cited by examiner

Primary Examiner—Kevin Truong
(74) Attorney, Agent, or Firm—Birch, Stewart, Kolasch & Birch, LLP

(57) ABSTRACT

A medical anesthetic needle which comprise an outside needle and a mandrin inserted into the outer needle to freely move in and out, and is slightly bent upward at is tip when its needle axis is positioned horizontal. The mandrin is manufacture by a first step of cutting the tip end of a metallic wire such as stainless steel wires obliquely to form a blade surface which intersects the axis at a predetermined angle of the mandrin blade surface, a second step of cutting off that portion of the metallic wire, which extends from the underside of the wire up to a horizontal plane located at a higher level than the center line of the wire, in a columnar region between the upper end of the blade surface and a position rearwardly distant three times the diameter of the wire or more from the upper end, to form a blade tip, a split-columnar connection succeeding the blade tip, and a columnar portion succeeding the connection, and a third step of bending the connection in such a manner that the upper end of the blade surface becomes higher a predetermined distance than the upper surface of the columnar portion and the axis of the blade tip is inclined at a predetermined angle (θ) relative to the horizontal, and cutting the entire length of the mandrin into a predetermined length.

8 Claims, 4 Drawing Sheets

MANDRIN OF MEDICAL ANESTHETIC NEEDLE AND METHOD OF MANUFACTURING SAME

This application is the national phase under 35 U.S.C. § 371 of PCT International Application No. PCT/JP97/02595 which has an International filing date of Jul. 28, 1997, which designated the United States of America.

TECHNICAL FIELD

The present invention relates to a medical anesthetic needle including a hollow outer needle having the front end thereof slightly bent upward from the needle axis when the needle axis is laid horizontal, and a solid inner needle being inserted into and through the outer needle from the rear thereof movably inward and outward.

BACKGROUND TECHNOLOGY

In operating an anesthetic needle having the axis of the front end thereof inclined upward from the needle axis, a human body is punctured or penetrated into with the anesthetic needle under the condition that a solid inner needle is inserted into and through a hollow outer needle thereof. Then, after the inner needle is drawn out, an instrument, such as a catheter for injecting anesthetic, is inserted instead. The reason for inserting the inner needle into and through the outer needle when the human body is penetrated into with the anesthetic needle, is to reinforce the outer needle, and, at the same time, to prevent human tissue from entering inside the outer needle.

The blade surfaces of the outer and inner needles intersect the axes of their respective front end portions at their respective predetermined blade surface angles. The blade surface of the inner needle is of a solid elliptic shape, and is fitted into the blade surface of a hollow elliptic shape located at the front end of the outer needle, approximately flush with the blade surface of the outer needle, to seal the opening of the blade surface of the hollow outer needle. In case, however, an entire front end portion of the inner needle was formed in the same shape and size as the hollow region of the front end portion of the outer needle having the front end thereof bent, then, the front end portion of the inner needle was not possible to insert into and through the outer needle from the rear end thereof. Thus, the front end portion of the inner needle used to be partially cut off so that the front end portion, as bent, of the inner needle is easily deformed elastically, thereby enabling the front end portion of the inner needle to insert into and through the outer needle from the rear end thereof.

Conventional inner needles used to be worked using a method shown in FIG. 6. The working method included a first step of bending the front end portion of a piece of stainless steel wire W having a diameter D approximately equal to the inner diameter of an outer needle, upward at a predetermined angle θ, relative to the horizontal, as shown in FIG. 6(a); a second step of cutting the piece of stainless steel wire W at a slant plane that passes through a point A located on the top surface line of a portion of the piece of stainless steel wire W bent upward, and higher than the top surface line of a portion of the piece of stainless steel wire W left straight and laid horizontal, by a predetermined distance h, and that intersects the axis of the portion of the piece of stainless steel wire W bent upward, at a predetermined angle θ, relative to the horizontal, to form a blade surface of the inner needle of a solid elliptic shape; and cutting the piece of stainless steel wire W to have the inner needle having an entire length equal to a predetermined length L, as shown in FIG. 6(b); and a third step of cutting off a portion of the piece of stainless steel wire, by means of machine cutting, that is located below a horizontal plane M passing through a position located at a height from the bottom surface of the piece of metallic wire greater than the radius of the piece of stainless steel wire, in a region located forward of a vertical plane passing through a position B located to the rear from the point A by a distance not less than three times the diameter D of the piece of stainless steel wire, when the piece of stainless steel wire has the axis thereof laid horizontal with the blade surface (5) placed facing upward, to form the inner needle 30, as shown in FIG. 6(c).

The first step of bending the piece of metallic wire W of a circular cross section, however, had a problem of generating many off-specification products, resulting in increased manufacturing cost, because of an extensive amount of springback being caused, thereby increasing dispersion in the inclination angle θ.

DISCLOSURE OF THE INVENTION

The present invention is made to solve the problem described above. Thus, an object of the present invention is to provide a solid inner needle that is capable of being inserted into and through an outer needle of a medical anesthetic needle having the front end thereof slightly bent, from the rear end of the outer needle movably inward and outward, and that has a shape enabling a great reduction in the manufacturing cost thereof.

An inner needle, according to the present invention, comprises: a blade tip portion having a blade surface that plugs the opening of a blade surface of a hollow outer needle having the front end thereof bent upward; a columnar portion having a diameter approximately equal to the inner diameter of the outer needle; and a connecting portion connecting the blade tip portion and the columnar portion together in one piece. The connecting portion is of a split-columnar shape, having the circular circumferential surface thereof extended flush to the circumferential surfaces of the blade tip portion and the columnar portion, having an axial length not less than three times the diameter of the columnar portion. The connecting portion has the bottom surface thereof positioned higher than the axis of the columnar portion, and is bent so that the upper end of the blade surface is located higher than the top surface line of the columnar portion by a predetermined distance and that the axis of the blade tip portion is inclined at a predetermined angle relative to the horizontal, when the inner needle has the axis thereof laid horizontal with the blade surface placed facing upward.

The inner needle described above, is manufactured using a method, when a piece of solid metallic wire having a diameter approximately equal to the inner diameter of the hollow outer needle, has the axis thereof laid horizontal, comprising: a first step of cutting the front end of the piece of metallic wire at a plane inclined at the same angle as the blade surface angle of the inner needle to form a blade surface of an elliptic shape; a second step of cutting off a portion of the piece of metallic wire that is located below a horizontal plane positioned at a height from the bottom surface of the piece of metallic wire greater than the radius of the piece of metallic wire, in a region located between the upper end of the blade surface and a position distant to the rear from the upper end of the blade surface by a distance not less than three times the diameter of the piece of metallic wire, to form a blade tip portion including the blade surface, and a connecting portion of a split-columnar shape; and a third step of bending the connecting portion so that the upper end of the elliptic-shaped blade surface is located higher than the horizontal top surface line of the columnar portion by a predetermined distance, and that the blade tip portion has the axis thereof inclined upward at a predetermined angle; and cutting the piece of metallic wire to have an entire length equal to a predetermined length.

The blade surface angle of the inner needle is preferably set to be equal to or slightly greater than the blade surface angle of the outer needle so that, when the elliptic-shaped solid blade surface of the inner needle is fitted into the elliptic-shaped hollow blade surface of the outer needle with the centers thereof aligned, the lower portion of the blade surface of the inner needle is prevented from protruding from the blade surface of the outer needle, thereby reducing pain caused by puncture.

The vertical width of the connecting portion of the inner needle is preferably made not more than 0.4 times the diameter of the columnar portion to improve precision in the bending work. When, for example, making the vertical width of the connecting portion approximately 0.2 times the diameter of the piece of metallic wire, the connecting portion becomes flat, which not only makes the bending work easy but also improves precision in the bending work, resulting in a very low ratio of off-specification product occurrence.

As described above, the inner needle of the present invention is bent upward in accordance with the front end portion of the outer needle, where the portion to be bent is not a columnar body having a circular cross section of prior art, but a flat split-columnar body having the vertical width or height smaller than the bottom side width thereof, and besides the bottom side width is smaller than the diameter of the circular cross section of prior art, thereby causing the amount of springback in the bending work to be very small compared with the cases of prior art. As a result, precision in the bending work is remarkably enhanced, the yield improves, and the manufacturing cost is sharply reduced.

The front end region of an inner needle manufactured in the way as described above, with the axis thereof laid horizontal and the blade surface thereof placed upward, comprises a blade tip portion having the blade surface, and a connecting portion extending from the rear end of the blade tip portion, having a split-columnar shape with a cross section of an area smaller than that of a semicircle, where the rear end of the connecting portion is connected to the columnar portion of the inner needle together in one piece. The circular circumferential surface of the connecting portion is extended flush to the circumferential surfaces of the blade tip portion and the columnar portion. The bottom surface of the connecting portion is at a position higher than the axis of the columnar portion. When inserting the inner needle into the outer needle from the rear of the outer needle, the blade tip portion having a diameter approximately equal to the inner diameter of the outer needle enters first, and the flat connecting portion follows. At this time, since the connecting portion deforms elastically, the columnar portion having a diameter approximately equal to the inner diameter of the outer needle that follows thereafter, is capable of being smoothly inserted into the outer needle.

When the blade tip portion is formed so that the rear end surface has the lower end thereof positioned axially forward relative to the upper end of the front end surface of the blade tip portion, thereby decreasing the axial length of the circumferential surface of the blade tip portion, then, the front end region of the inner needle is enabled to move through the hollow region of the outer needle further smoothly.

BEST EMBODIMENTS OF THE INVENTION

Figure 1:
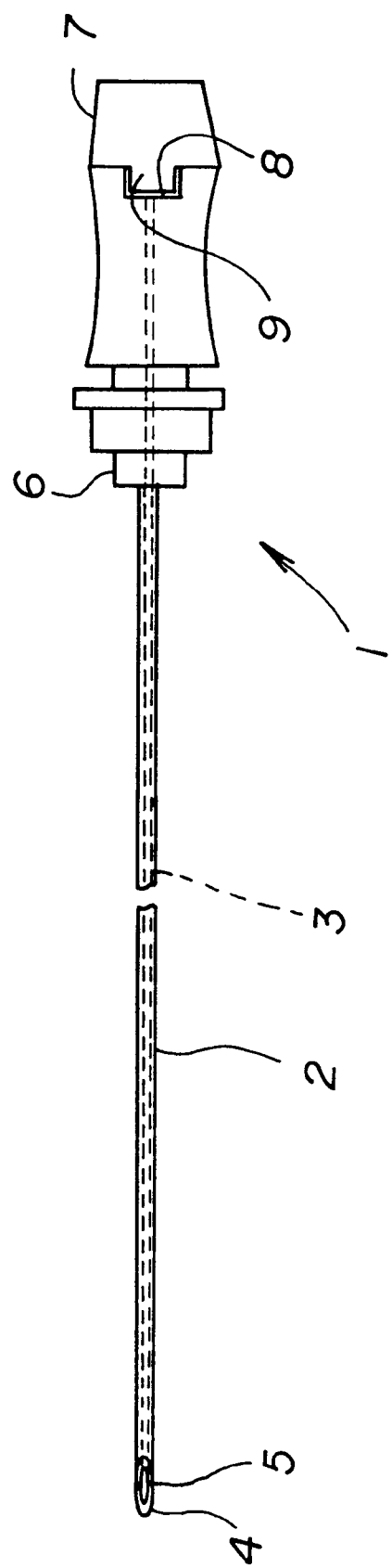
FIG. 1 is a plan view showing a medical anesthetic needle of the present invention, as somewhat enlarged.

As shown in FIG. 1, an anesthetic needle 1 includes a hollow outer needle 2 made of stainless steel tube and a solid inner needle 3 made of stainless steel bar. The inner needle 3 is inserted into and through the outer needle from the rear end thereof movably inward and outward. The outer needle 2 and the inner needle 3 have a blade surface 4 of a hollow elliptic shape and a blade surface 5 of a solid elliptic shape formed at the front ends thereof, respectively. The rear ends of the outer needle 2 and the inner needle 3 are fixed to a needle base 6 made of plastics, and to a knob 7, together, respectively. A recess 8 and a protrusion 9 are formed on the rear end surface of the needle base 6 and the front end surface of the knob 7, respectively. When the protrusion 9 of the knob 7 is fitted into the recess 8 of the needle base 6, the blade surface 4 of the outer needle 2 and the blade surface 5 of the inner needle 3 come approximately flush. The anesthetic needle is punctured or penetrated into a human body with, under the condition that the protrusion 9 of the knob 7 is fitted into the recess 8 of the needle base 6. The inner needle 3 inserted into and through the outer needle 2, reinforces the hollow outer needle 2 of a relatively thin wall thickness, thereby preventing the outer needle 2 from breakage.

Figure 2:
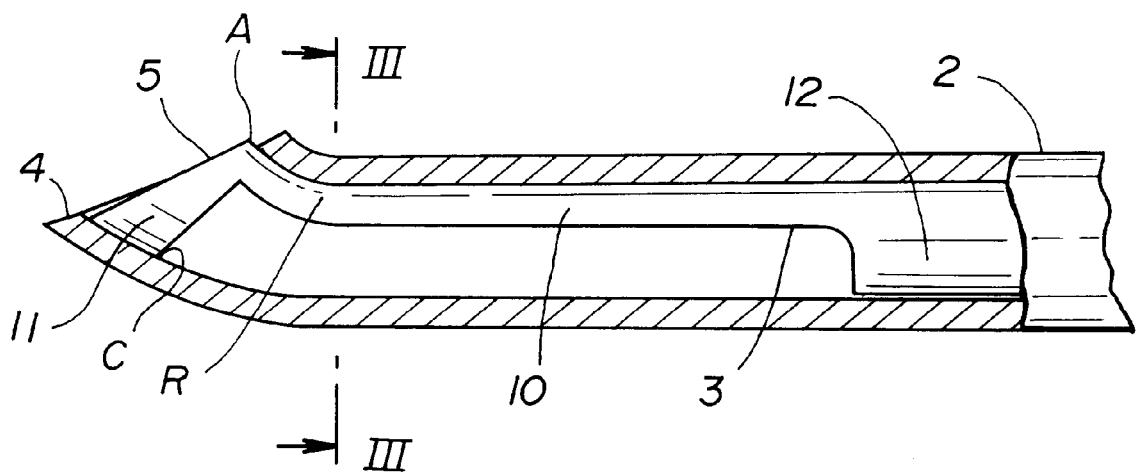
FIG. 2 is a longitudinal sectional view showing the front end section of the medical anesthetic needle of FIG. 1, as further enlarged.

As shown in FIG. 2, when the needle axis is laid horizontal with the blade surfaces 4 and 5 placed facing upward, the front end section of the outer needle 2 is bent upward. The front end section of the inner needle 3 includes a blade tip portion 11 of a shape of a column slantly cut off, and a connecting portion 10 extending from the rear of the blade tip portion, having a split-columnar shape with a cross section of an area smaller than that of a semicircle. From the rear end of the connecting portion 10 extends a columnar portion 12 of a diameter approximately equal to the inner diameter of the outer needle 2.

The elliptic-shaped outer end surface of the blade tip portion 11 is the blade surface 5 that intersects the axis of the blade tip portion 11 at a predetermined blade surface angle. When the blade surface 5 of the inner needle 3 is fitted into the elhptic-shaped hollow blade surface 4 of the outer needle 2, the blade surfaces 4 and 5 are concentric with each other. However, since the blade surface angle of the inner needle 3 is slightly greater than the blade surface angle of the outer needle 2, the lower-half part of the blade surface of the inner needle sinks below the blade surface of the outer needle, which prevents the double-blade phenomenon from occurring at the blade tip, thereby reducing the puncture pain. When the anesthetic needle 1 is punctured or penetrated into a human body with, the blade tip portion 11 of the inner needle 3 completely seals the opening inside the blade surface 4 of the outer needle 2, thereby preventing human tissue from entering the hollow region inside the outer needle 2.

The axial length of the connecting portion 10 is not less than three times the diameter of the columnar portion 12. The connecting portion 10 has a curvature region R located near the front end thereof. By means of the curvature R, the circular circumferential surface of the connecting portion 10 is in contact with the upper inner surface of the outer needle 2. The circular circumferential surface is extended flush to the circumferential surface of the blade tip portion 11 at the rear end thereof, and flush to the circumferential surface of the columnar portion 12, respectively.

The lower end C of the rear end surface of the blade tip portion 11 is positioned axially forward relative to the upper end of the blade surface 5, i.e., the upper end A of the front end surface of the blade tip portion 11, where the axial length of the circumferential surface of the blade tip portion 11 is very short compared with the diameter of the blade tip portion 11.

Figure 3:
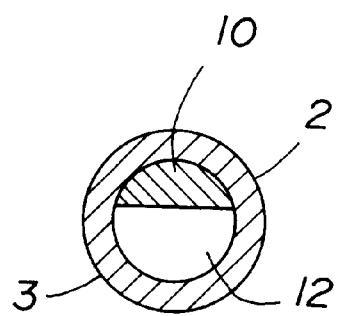
FIG. 3 is a cross-sectional view along arrow lines III—III of FIG. 2.

As shown in FIG. 3, the cross section of the connecting portion 10 within the outer needle 2 is a split-circular shape having the same radius of curvature as the radius of the columnar portion 12 of the inner needle 3, where the bottom side of the split-circular cross section is horizontal, and the height thereof is 0.2–0.4 times the diameter of the columnar portion 12.

Figure 4:
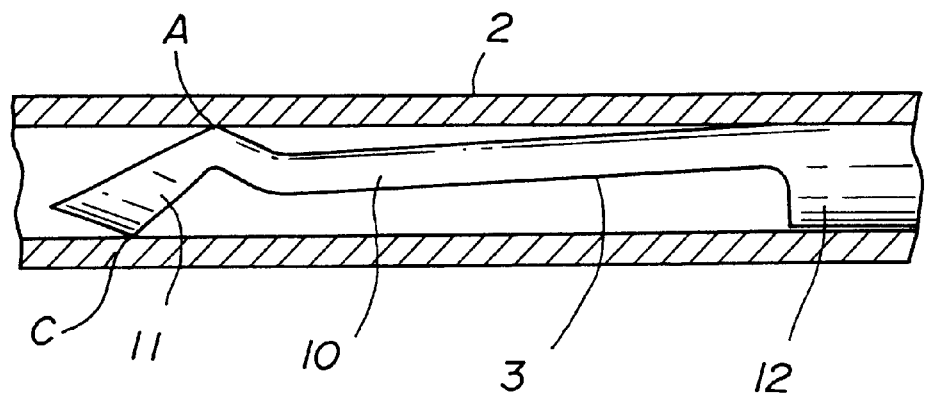
FIG. 4 is an enlarged longitudinal partial sectional view of an anesthetic needle, showing the front end section of an inner needle moving through an outer needle.

As shown in FIG. 4, when the front end section moves through the straight hollow region of the outer needle 2, the lower end C of the rear end surface of the blade tip portion 11 is positioned axially forward relative to the upper end A of the front end surface of the blade tip portion 11, and the connecting portion 10 deforms elastically, whereby the blade tip portion 11 and the columnar portion 12 move smoothly.

Figure 5:
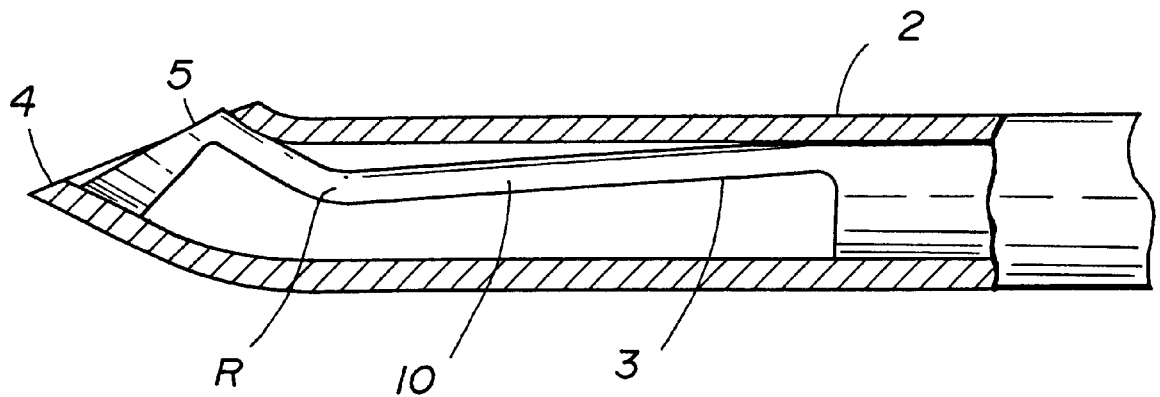
FIG. 5 is a view corresponding to FIG. 2, of another embodiment

As shown in FIG. 5, the curvature region R may be located farther to the rear of the position shown in FIG. 2. In this case, when the blade surface 5 of the inner needle 3 is fitted into the blade surface 4 of the outer needle 2, the upper surface of the connecting portion 10 does not come in contact with the upper inner surface of the outer needle 2, thereby causing a gap therebetween. However, farther apart from the front end of the connecting portion 10 the curvature R is, the easier the bending work becomes.

Next, the manufacturing process of the inner needle will be discussed, according to the present invention.

Figure 6:
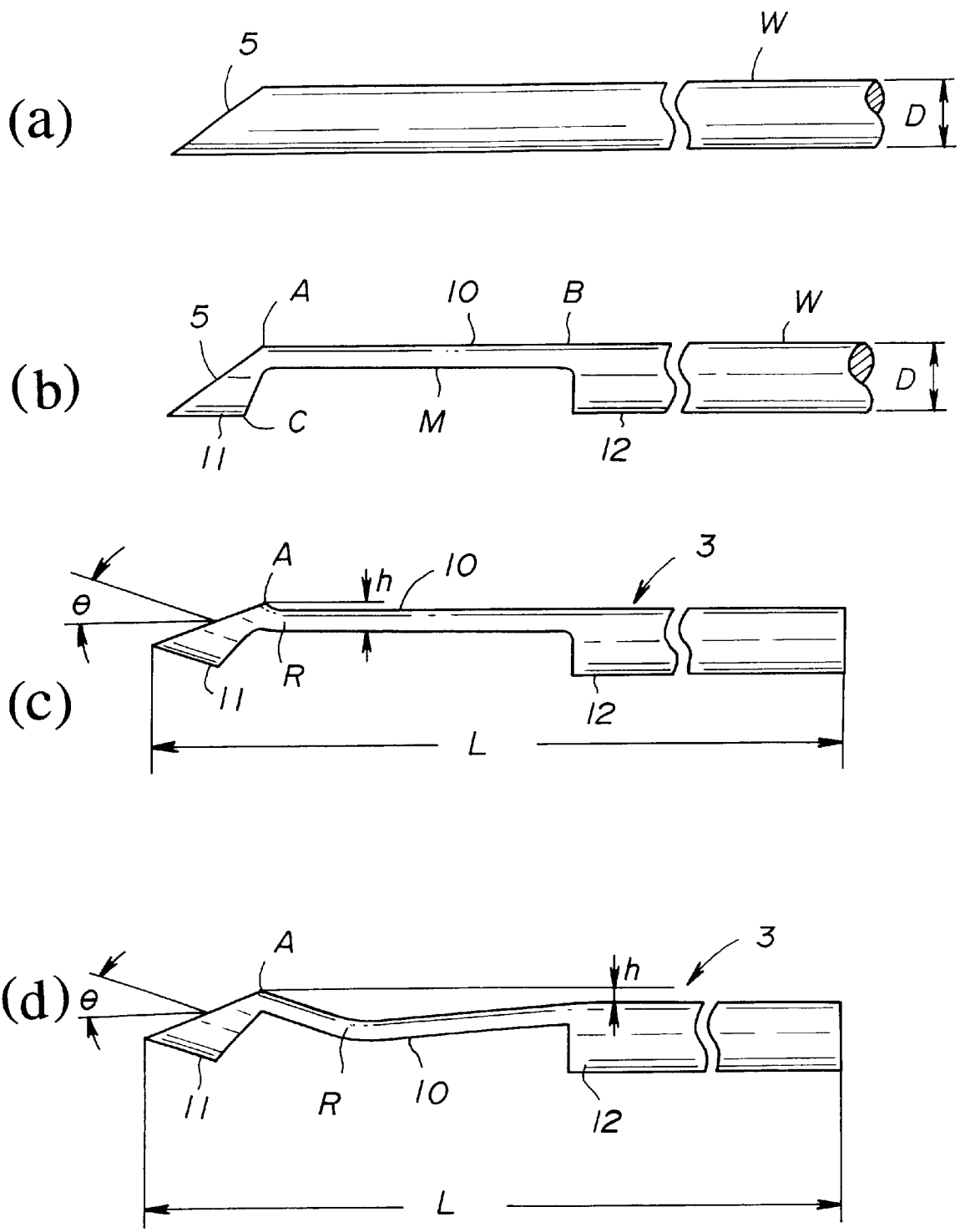
FIG. 6 is a set of views showing a process of manufacturing the inner needle of FIG. 1.

The inner needle may be manufactured from a piece of stainless steel wire having a diameter approximately equal to the inner diameter of the outer needle, using the process shown in FIG. 6.

In the first step of the process shown in FIG. 6(a), the tip of a piece of stainless steel wire W having a diameter approximately equal to the inner diameter of the outer needle, is slantly cut to form, at the front end thereof, a blade surface 5 intersecting the axis of the piece of stainless steel wire at a blade surface angle of the inner needle. The blade surface angle of the inner needle is set equal to or slightly greater than the blade surface angle of the outer needle 2.

In the second step of the process shown in FIG. 6(b), a portion of the piece of stainless steel wire is cut off, which portion is located below a horizontal plane M positioned a little higher than the axis of the piece of stainless steel wire, in between the upper end A of the blade surface, or a position slightly to the rear thereof, and a position B located to the rear from the upper end (A), or that position, by a distance not less than three times the diameter D, to form a blade tip portion 11 at the front end, and a connecting portion 10 of a split-columnar shape extending from the blade tip portion 11. From the rear end of the connecting portion 10 extends a columnar portion 12 having a diameter D. The cross section of the connecting portion 10 is a split-circular shape having a bottom side thereof positioned horizontal, where the height thereof is not more than one half of the diameter D of the piece of stainless steel wire, for example, 0.2–0.4 times the diameter D.

When cutting off the portion below the horizontal plane M of the stainless steel wire, the front end position of the portion to be cut off is moved forward as the front end position of the portion moves downward so that the axial distance between the foremost end of the blade tip portion 11 and the lower end C of the rear end circumferential edge of the blade tip portion 11 is shorter than the axial distance between the foremost end of the blade tip portion 11 and the upper end A of the front end circumferential edge of the blade tip portion 11. By this, the axial length of the circumferential surface of the blade tip portion 11 is shortened, resulting in smooth and easy insertion of the inner needle into the outer needle being enabled.

In the third step shown in FIG. 6(c) or FIG. 6(d), the connecting portion 10 is bent so that the upper end A of the blade tip portion 11 is located higher than the top surface of the columnar portion 12 by a predetermined distance h, and that the axis of the blade tip portion 11 has a predetermined inclination angle θ; and cutting the piece of stainless steel wire to have an entire length equal to a predetermined length L, to obtain an inner needle 3. The connecting portion 10 is vertically flat and thin, whereby the amount of springback caused is small, which in turn makes the bending work easy. As a result, precision in the bending work is improved, and dispersion in the inclination angle θ is very little. Therefore, the off-specification product occurrence is reduced, and a great reduction is implemented in the manufacturing cost of such inner needles.

FIG. 6(c) shows a case of the connecting portion 10 being bent so that the circular circumferential surface of the connecting portion 10 is located along the inner circumferential surface of the outer needle 2, where the curvature region R is located near the front end of the connecting portion 10.

FIG. 6(d) shows a case where the curvature region R is located farther to the rear of the position shown in FIG. 6(c). In this case, the upper surface of the connecting portion 10 is not located along the inner circumferential surface of the outer needle 2. However, bending work is easier than in the case of FIG. 6(c).

What is claimed is:
1. A medical anesthetic needle which comprises
a hollow outer needle having a front end portion bent in an upward direction, said front end portion terminating in a hollow blade surface opening,
an inner needle having a solid blade tip portion containing a blade surface that plugs the hollow blade surface opening of the hollow outer needle, said inner needle having a front end portion bent in an upward direction, a columnar portion having a diameter approximately equal to the inner diameter of the hollow outer needle and a connecting portion connecting the tip portion and the columnar portion together as one piece, said connecting portion having a split-columnar shape, with the circular circumferential surface thereof extended flush to the circumferential surfaces of said blade tip portion and said columnar portion, and having an axial length not less than three times said diameter, said connecting portion having the bottom surface thereof positioned higher than the axis of said columnar portion when said inner needle has an axis thereof laid horizontal with said blade surface positioned facing upward, said connecting portion being bent so that an upper end of said blade surface is located higher than the top surface line of said columnar portion by a predetermined distance and said solid blade tip portion has an axis which is inclined at a predetermined angle, relative to horizontal, when the inner needle has its axis laid horizontal with said blade surface positioned facing upward.

2. The medical anesthetic needle according to claim 1, wherein the connecting portion has a split-circular cross section with a height from a bottom horizontal said thereof of not less than 0.2 times and not more than 0.4 times the diameter.

3. The inner needle of a medical anesthetic needle according to claim 2, wherein the solid blade tip portion has a rear end surface thereof inclined, with the lower part of said rear end surface positioned forward relative to an upper end of a front end surface of said solid blade tip portion.

4. The medical anesthetic needle according to claim 1, wherein the solid blade tip portion has a rear end surface thereof included, with the lower part of said rear end surface positioned forward relative to an upper end of a front end surface of said solid blade tip portion.

5. A method of manufacturing a medical anesthetic needle which comprises forming an inner needle by slantly cutting a front end of a piece of metallic wire at a predetermined surface angle to form a blade surface, said piece of metallic wire having an axis and a diameter approximately equal to an inner diameter of a hollow outer needle having a front end portion thereof bent in the upward direction, cutting out a section of said piece of metallic wire that is located below a horizontal plane positioned higher than the axis of said piece of metallic wire, between an upper end of said blade surface and a position located to the rear from said upper end by a distance not less than three times the diameter of said metallic wire when said piece of metallic wire has the axis thereof laid horizontal with said blade surface positioned facing in the upward direction, to form, from said piece of metallic wire, a blade tip portion having said blade surface as the front end surface thereof, a connecting portion of a split-columnar shape extending rearward from said blade tip portion, and a columnar portion extending rearward from said connecting portion;

bending said connecting portion so that the upper end of said blade surface is located higher than the top surface line of said columnar portion by a predetermined distance, said blade tip portion having an axis which is inclined at a predetermined angle relative to the horizontal, and cutting said piece of metallic wire to have an entire length equal to a predetermined length.

6. The method of manufacturing the medical anesthetic needle according to claim 5, wherein the connecting portion has a vertical width of not less than 0.2 times and not more than 0.4 times the diameter.

7. The method of manufacturing the medical anesthetic needle according to claim 6, wherein the second step includes cutting out a section of said piece of metallic wire so that said blade tip portion has a rear end surface thereof inclined, with the lower part of said rear end surface positioned forward relative to an upper end of a front end surface of said solid blade tip portion.

8. The method of manufacturing the medical anesthetic needle according to claim 5, wherein the second step includes cutting out a section of said piece of metallic wire so that said blade tip portion has a rear end surface thereof inclined, with the lower part of said rear end surface positioned forward relative to an upper end of a front end surface of said solid blade tip portion.

* * * * *